United States Patent [19]

Eidschun

[11] 4,393,705

[45] Jul. 19, 1983

[54] SPECIFIC GRAVITY LEVEL GAUGE AND METHOD

[75] Inventor: Charles D. Eidschun, Clearwater, Fla.

[73] Assignee: Micro-Plate, Inc., Clearwater, Fla.

[21] Appl. No.: 287,246

[22] Filed: Jul. 27, 1981

[51] Int. Cl.³ .............................................. G01N 9/28
[52] U.S. Cl. ......................................... 73/439; 73/299
[58] Field of Search .......................... 73/439, 299, 302

[56] References Cited

U.S. PATENT DOCUMENTS

| | | | |
|---|---|---|---|
| 3,038,336 | 6/1962 | Peters | 73/299 |
| 3,427,198 | 2/1969 | Hill | 73/439 |
| 3,453,891 | 7/1969 | Kapff et al. | 73/439 |
| 3,460,394 | 8/1969 | Cryer | 73/439 |
| 3,911,741 | 10/1975 | Rochon et al. | 73/439 |
| 4,291,575 | 9/1981 | Frissora | 73/302 |

Primary Examiner—Howard A. Birmiel
Attorney, Agent, or Firm—Jack E. Dominik

[57] ABSTRACT

Disclosed is an apparatus which utilizes pipes of different lengths oriented vertically within the fluid of a reservoir which are constantly pressured with a gas source, normally air. Since the pipes are of different length, but the pressure is the same, a different back pressure will occur in the longer pipe as compared to the shorter pipe due to the differing head of fluid which must be displaced by the gas to slowly bubble out of the lower end of the pipes. This pressure differential is then read and the calculations applied, either from a table or constantly monitored through a computer, to measure the pressure differential and calculate the same in terms of specific gravity. Once the specific gravity is known, the back pressure on either the short pipe or the long pipe can be impairedly calibrated, or calculated by an equation having the specific gravity now known, and then determining from that the back pressure which will vary with the height of the fluid in the reservoir. The apparatus includes an enclosure, a dome-like plenum chamber, and pressure chambers which are connected directly to a short pipe and a long pipe. Bleed holes are provided at the top of the pressure chambers of the size of a hypodermic needle to constantly permit the gaseous fluid to flow from the plenum into the long and short tube, and pressure transducers are directly coupled to the pressure chambers to provide a constant read-out.

5 Claims, 3 Drawing Figures

SPECIFIC GRAVITY LEVEL GAUGE AND METHOD

FIELD OF INVENTION

The present invention relates to the measurement of specific gravity of a fluid and at the same time measuring the level of the fluid. More specifically the device and method are directed to a constant air flow to pipes of different levels within the fluid, the specific gravity being first calculated by the pressure differential between the two heads of fluids, and once the specific gravity is known, the pressure in either one of the fluid tubes can be used to calculate out the level within a reservoir.

PRIOR ART

The prior art for measuring the specific gravity of a fluid has essentially been by employing a hydrometer which directly determines by a flotation measurement the specific gravity. Where the corrosive environment of plating solutions is involved, hydrometers can become encrusted with mineral salts and therefore their buoyancy change, with a consequent inaccuracy in the measurement. In addition, where electrical conductivity is measured, the electrodes can themselves, in a corrosive fluid, become corroded and the conductivity altered, and as a consequence the reading will be inaccurate.

SUMMARY

The present invention is directed to an apparatus which utilizes pipes of different lengths oriented vertically within the fluid of a reservoir which are constantly pressured with a gas source, normally air. Since the pipes are of different length, but the pressure is the same, a different back pressure will occur in the longer pipe as compared to the shorter pipe due to the differing head of fluid which must be displaced by the gas to slowly bubble out of the lower end of the pipes. This pressure differential is then read and the calculations applied, either from a table or constantly monitored through a computer, to measure the pressure differential and calculate the same in terms of specific gravity. Once the specific gravity is known, the back pressure on either the short pipe or the long pipe can be empirically calibrated, or calculated by an equation having the specific gravity now known, and then determining from that the back pressure which will vary with the height of the fluid in the reservoir. The apparatus includes an enclosure, a dome-like plenum chamber, and pressure chambers which are connected directly to a short pipe and a long pipe. Bleed holes are provided at the top of the pressure chambers of the size of a hypodermic needle to constantly permit the gaseous fluid to flow from the plenum into the long and short tube, and pressure transducers are directly coupled to the pressure chambers to provide a constant read-out.

In view of the foregoing, it is a principal object of the present invention to provide a mechanism and method for reading the specific gravity of a fluid which can be the subject of constant readings.

Yet another object of the present invention is to provide a specific gravity and level measuring gauge which, because it relies on the bleading of air or other gaseous fluid, is self purging and self cleaning in a corrosive environment.

Yet another object of the present invention is to provide a specific gravity level gauge and method which is relatively inexpensive to manufacture, and yet durable and simplistic in its operation.

DESCRIPTION OF THE DRAWINGS

Further objects and advantages of the present invention will become apparent as the following description of an illustrative embodiment proceeds, taken in conjunction with the accompanying drawings, in which.

DESCRIPTION OF PREFERRED EMBODIMENT

Figures 1, 2:
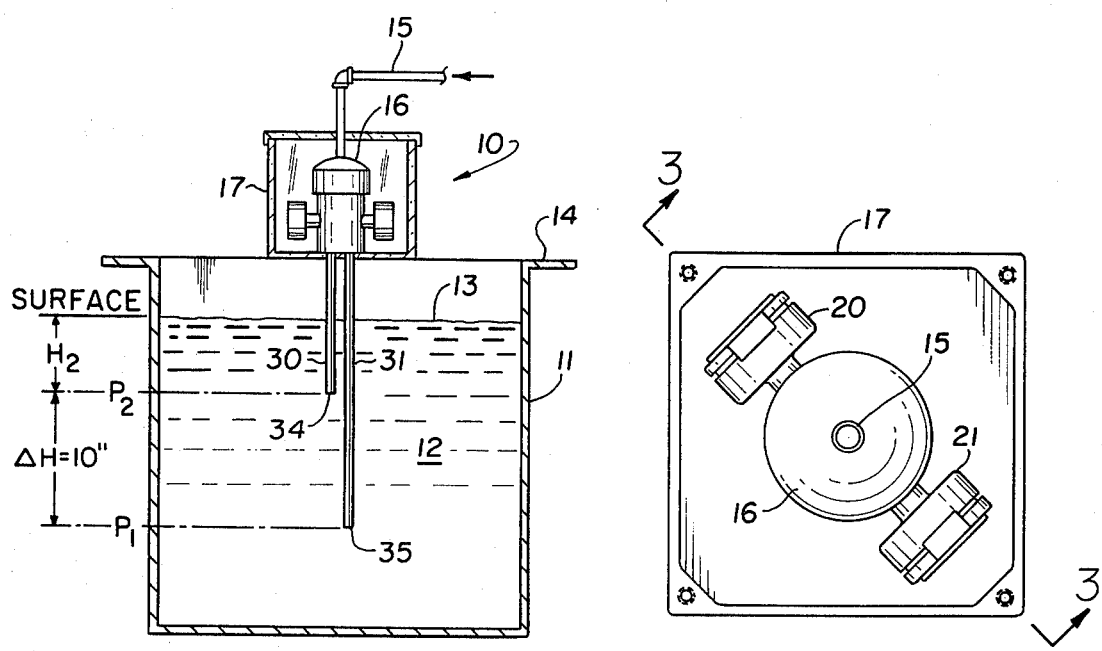
FIG. 1 is a transverse sectional view of a typical reservoir, partially diagrammatic, indicating the installation of the specific gravity level gauge and the relative relationship of its parts.
FIG. 2 is a top view of the interior of the enclosure of the specific gravity level gauge and showing the positioning of the pressure transducers.

The specific gravity level gauge 10 illustrative of the present invention is used in connection with a reservoir 11 which contains a fluid 12. The level 13 of the fluid 12 will vary upwardly and downwardly within the reservoir 11. The specific gravity of the fluid, typically employed in a plating environment, will vary from time to time and is monitored to determine that it is constantly within the allowable limits for effective plating. While the invention is not limited to a plating environment, it is a highly desirable apparatus and method for such fluids. The reservoir contains normally a mounting flange 14 about its upper portion.

Figure 3:
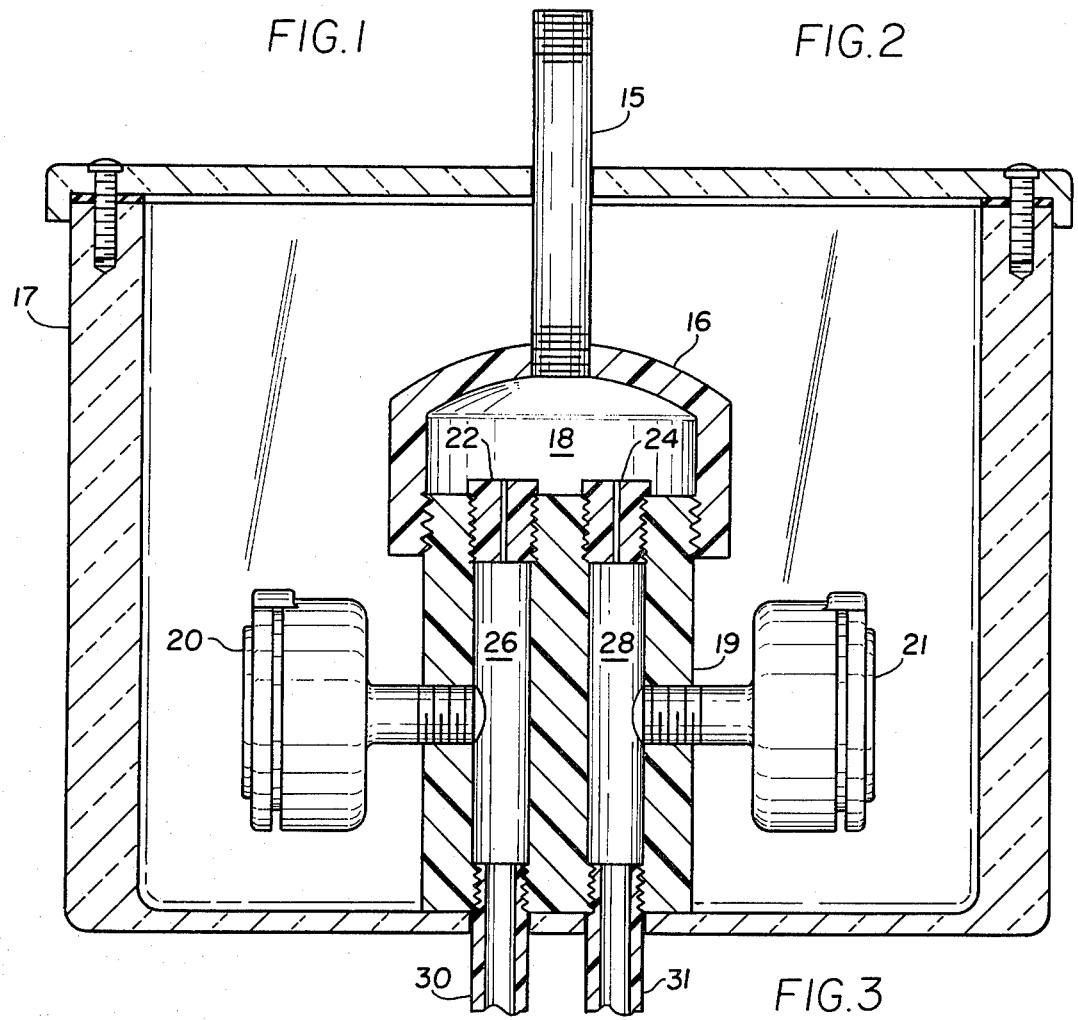
FIG. 3 is a transverse sectional view in enlarged scale of the interior portion of the enclosure taken along section line 3—3 of FIG. 2.

As noted in FIGS. 1 and 3, an air line 15 is fed to a plenum dome 16 all encased in the enclosure 17. The plenum 18 is interior of the plenum dome 16. To be noted is that the plenum dome 16 is coupled in gas-tight relationship to the gauge body 19. A pressure transducer 20 is provided for the short pipe, and a pressure transducer 21 for the long pipe. Immediately atop the gauge body 19 provision is made for pressure bleeds 22, 24 which are shown as plugs, and drilled with a hole approximately the diameter of a hypodermic needle or 0.010 inches. The pressure bleeds 24, 26 lead directly into the pressure chamber 26 for the short pipe, and the pressure chamber 28 for the long pipe. As noted, the short pipe 30 is shown in FIG. 3 on the left-hand side and the long pipe 31 is shown on the right side. Each of the pipes terminate in a short pipe end 34 and a long pipe end 35.

In operation, as indicated above, air or another gas is permitted to pass through the air line 15 into the plenum 18, through the pressure bleed holes 22, 24 and into the pressure chambers 26, 28. Once the unit stabilizes with a small amount of bubbling at the lower ends 34, 35 of the short pipe and the long pipe, the stabilized pressure in the short pressure chamber 26 and long pressure chamber 28 are read by their respective pressure transducers 20, 21. The calculations are then performed to determine the specific gravity of the fluid 12 as well as the fluid level 13 based upon pressure differentials between the short pipe 30 and the long pipe 31 and thereafter directly determined by the absolute pressure reading on either the short pipe 30 or the long pipe 31.

THE METHOD

The present method stems from the known fact that with a given head differential anyplace within a fluid, the amount of pressure required to support that head differential can be calculated into the specific gravity of the fluid. The formula is set forth below, and correlative letters are applied to FIG. 1;

P1 is the measured pressure of a point near the bottom of the reservoir, namely the bottom of long pipe 31. H1 is the distance from the fluid surface level to the point at which P1 is measured.

P2 is the measured pressure of a point 10 inches (example) closer to the surface, namely the bottom of short pipe 30. H2 is the distance from the fluid surface level to the point at which P2 is measured. Therefore:

$$P1 = dh1 \tag{1}$$

$$P2 = dH2 \tag{2}$$

subtracting equation 2 from 1 yields:

$$P1 - P2 = d(H1 - H2) \tag{3}$$

or $$d = (P1 - P2)/(H1 - H2)$$

where
- d = density in lb/in$^3$
- P = gauge pressure in lb/in$^2$
- H = depth below surface in inches Once the density has been determined, then either H1 or H2 can be determined from equations (1) or (2) from which liquid level may be determined. In some instances, liquid level may be determined from a single pressure transducer if the density of the liquid is known or consistent or if the level accuracy requirements are not too severe. The method therefore basically contemplates the steps of positioning two lengths of pipes in a given fluid, supplying the same with a given amount of gaseous fluid and flowed into the pipes so that a stabilization or slow bubbling will occur at the bottom of the pipes, and thereafter the pressures of the gaseous fluid on the two different pipes will have a differential which can be read-out, and through suitable calculations the specific gravity and subsequently the level of the fluid determined.

Although particular embodiments of the invention have been shown and described in full here, there is no intention to thereby limit the invention to the details of such embodiments. On the contrary, the intention is to cover all modifications, alternatives, embodiments, usages and equivalents of a specific gravity level gauge, as fall within the spirit and scope of the present invention, specification, and appended claims.

I claim:

1. A specific gravity and level gauge comprising, in combination,
   a pair of pipes for insertion into a liquid fluid having a variable level and variable specific gravity, the length of the pipes being predetermined to provide a head differential between the lower end of the shorter pipe and the lower end of the longer pipe,
   means for securing the pipes in essentially vertically oriented fashion with the liquid fluid to be measured,
   means for supplying a gaseous fluid into each of the pipes including a plenum to maintain a given head of gaseous fluid by slowly discharging the gas into the liquid fluid at the lower end portion of the pipes,
   a pair of gaseous fluid pressure chambers at the upper portion of the pipes,
   bleed holes for permitting a gaseous fluid to pass from the plenum into the gaseous pressure fluid chambers and thence to the pipes,
   and pressure transducer means for reacing the gaseous pressure fluid in the pressure chamber for the short pipe and the gaseous pressure fluid chamber for the long pipe.

2. In the specific gravity level gauge of claim 1,
   enclosure means for housing the upper portion of the pipes, transducer, and plenum including bracket means for securing the same to a reservoir containing a liquid fluid to be measured.

3. In the specific gravity level gauge of claim 1,
   the bleed holes for the gaseous fluid in the plenum to the gaseous pressure chambers having an identical diameter of hole.

4. The method of measuring the specific gravity and level within a liquid fluid reservoir, comprising the steps of
   supplying a gaseous pressure of a given amount to a pair of vertical pipes positioned at different depths within the liquid fluid reservoir,
   providing a pair of pressure chambers at the upper portion of the pipes with bleed holes leading a source of uniform gaseous fluid pressure,
   bringing the supply of the gaseous fluid into a stabilized relationship in a plenum in gas communication with the bleed holes so that the vertical pipes of different depths are essentially filled with the gaseous fluid and essentially free of the liquid fluid which is to be measured,
   once stability is achieved, measuring the gaseous fluid pressure in each of the pipes,
   thereafter utilizing the differential in pressure along with the known of the differential head of the two pipes to calculate the specific gravity of the liquid fluid.

5. In the method of claim 4 above,
   the additional step of applying the specific gravity to the gaseous fluid pressure measured on either the deeper pipe or the shallower pipe, and thereafter calculating the level of the fluid contained within the reservoir.

* * * * *